(12) United States Patent
Graham et al.

(10) Patent No.: US 7,766,480 B1
(45) Date of Patent: Aug. 3, 2010

(54) GONIO LENS WITH GEOMETRIC REFERENCE

(75) Inventors: Raymond D. Graham, Renton, WA (US); Sungjun J. Hwang, Victor, NY (US); Mark A. Latina, North Andover, MA (US)

(73) Assignee: Ocular Instruments, Inc., Bellevue, WA (US)

( * ) Notice: Subject to any disclaimer, the term of this patent is extended or adjusted under 35 U.S.C. 154(b) by 0 days.

(21) Appl. No.: 12/505,346

(22) Filed: Jul. 17, 2009

(51) Int. Cl.
*A61B 3/00* (2006.01)
*A61B 3/10* (2006.01)

(52) U.S. Cl. ...................... 351/219; 351/221
(58) Field of Classification Search .......... 351/219, 351/221, 205, 246, 247, 160 R, 160 H, 159; 606/4, 6, 18
See application file for complete search history.

(56) References Cited

U.S. PATENT DOCUMENTS 4,134,647 A * 1/1979 Ramos-Caldera ........... 351/219
5,255,025 A * 10/1993 Volk ........................... 351/205
7,125,119 B2 * 10/2006 Farberov ..................... 351/219

OTHER PUBLICATIONS

Boys-Smith, J.W., "Boys-Smith Pigment Gradation Laser Lens," © 1984, Ocular Instruments, Inc., Bellevue, Wash., 3-page brochure.

* cited by examiner

*Primary Examiner*—Hung X Dang
(74) *Attorney, Agent, or Firm*—Christensen O'Connor Johnson Kindness PLLC

(57) ABSTRACT

A gonio lens is provided including a contact lens element and a geometric reference member. The contact lens element has an optical axis, a concave posterior contact surface to be placed in optical contact with the cornea of a patient's eye, and an anterior surface. The geometric reference member, such as a scale, is provided near the concave posterior contact surface of the contact lens element. The configuration and location of the geometric reference member are chosen to provide an image of the geometric reference member adjacent to an image of the periphery of the anterior chamber of the eye of a patient within a field of view of the contact lens element when the contact lens element is placed on the eye of a patient. The two images are formed relative to each other such that they are simultaneously in focus to permit visual comparison between the two.

20 Claims, 8 Drawing Sheets

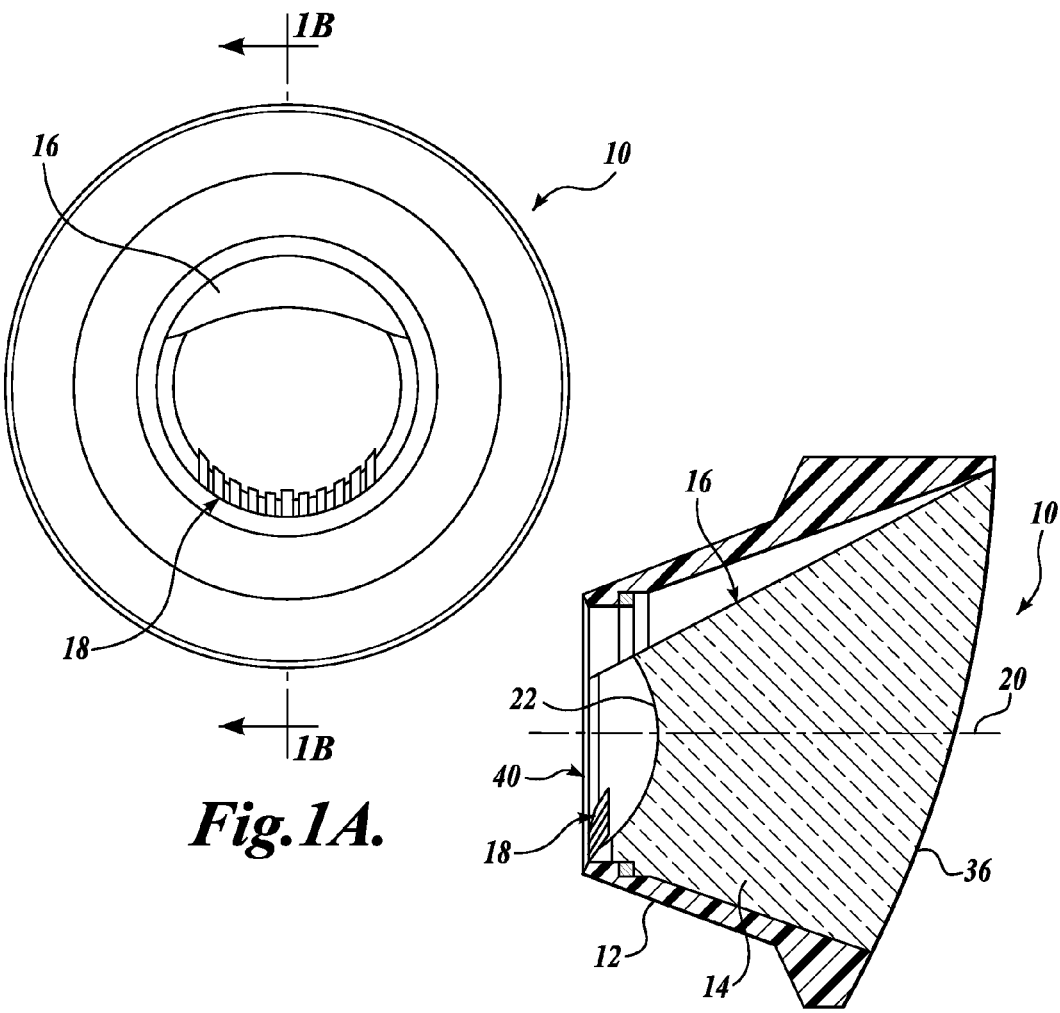
Fig.1A.
Fig.1B.
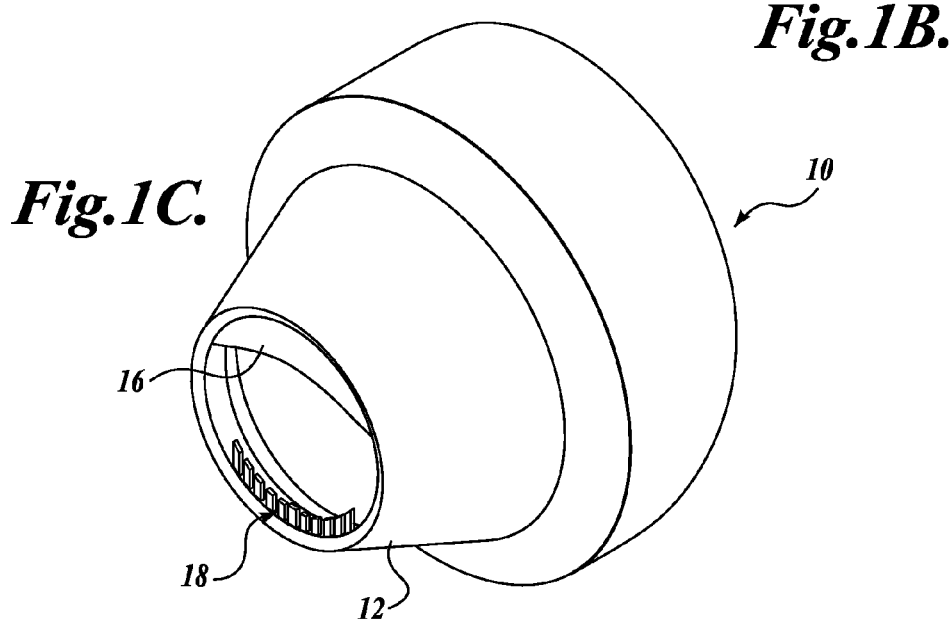
Fig.1C.

GONIO LENS WITH GEOMETRIC REFERENCE

FIELD OF THE INVENTION

The present invention relates to lenses utilized in the examination and treatment of the eye and, more particularly, to lenses utilized in viewing the periphery of the anterior chamber of the eye.

BACKGROUND

A lens utilized in connection with gonioscopy, i.e., the viewing of the periphery of the anterior chamber of the eye, is known as a gonio lens or gonioscope. A gonio lens generally includes a contact lens element and one or more mirrors. The contact lens element has an optical axis and a concave posterior contact surface that conforms to the anterior surface of the cornea of an eye. The contact lens element also has an anterior surface that is offset in an anterior direction from the contact surface. At least one mirror is arranged with its planar surface angled away from the optical axis of the contact lens element in an anterior direction. When the contact lens element is positioned on the eye, the mirror(s) reflect the light from the periphery of the anterior chamber of the eye into the direction of the observer, typically via a microscope for necessary magnification. The observer can thus study an image of the periphery of the anterior chamber to assess, for example, the iridocorneal angle, i.e., the angle formed by the cornea and the iris of an eye, or the trabecular meshwork located around the base of the cornea. For example, the observer can visually assess any inflammation or structural defects in the trabecular meshwork and related adjacent structures in the eye. As another example, using a gonio lens that is configured for the dual purposes of viewing and treating an eye, such as an iridotomy goniolaser lens and a trabeculoplasty goniolaser lens (e.g., a Selective Laser Trabeculoplasty lens or SLT lens), the observer may assess the trabecular meshwork before, during, and after the treatment with laser energy to thereby assess the efficacy of the treatment.

SUMMARY

This summary is provided to introduce a selection of concepts in a simplified form that is further described below in the Detailed Description. This summary is not intended to identify key features of the claimed subject matter nor is it intended to be used as an aid in determining the scope of the claimed subject matter.

It would be desirable for the observer of a gonio lens to be able to make geometric assessment or measurements of the image of the periphery of the anterior chamber of the eye. For example, the observer may wish to determine the size or shape of any defects visible in the image or the relative distance between two or more points in the image. The present invention is directed to providing a gonio lens that permits such geometric assessment and measurements by the observer.

According to various exemplary embodiments of the present invention, a gonio lens is provided including a contact lens element, one or more mirrors, and a geometric reference member. The contact lens element has an optical axis, a concave posterior contact surface to be placed in optical contact with the cornea of a patient's eye, and an anterior surface. At least one mirror is offset from the optical axis of the contact lens element and includes a planar surface that is angled away from the optical axis as the planar surface extends in an anterior direction. The geometric reference member, such as a scale, is provided near the concave posterior contact surface of the contact lens element. The configuration and location of the geometric reference member are chosen to provide an image of the geometric reference member adjacent to an image of the periphery of the anterior chamber of the eye of a patient within a field of view of the contact lens element when the contact lens element is placed on the eye of a patient. The two images are formed relative to each other such that they are simultaneously in focus to permit visual comparison between the two. Accordingly, the observer can readily determine the size or shape of any artifacts in the image of the periphery of the anterior chamber or the relative distance between two or more points in such image.

In accordance with other embodiments of the present invention, a gonio lens includes a contact lens element and a geometric reference member as with the previously described embodiments, but does not include any mirror. In operation, the light rays from the periphery of the anterior chamber propagate directly toward the observer. As with the previously described embodiments, the observer can then compare the image of the periphery of the anterior chamber relative to the image of the geometric reference member, to thereby determine the size or shape of any artifacts in the image of the periphery of the anterior chamber or the relative distance between two or more points in the image.

The geometric reference member may be a scale including a series of linear, circular, or polar markings. The geometric reference member may also consist of a single marking, such as a bar. Further alternatively, the geometric reference member may include a rectangular grid or a polar grid. The specific configuration of a geometric reference member may be chosen depending on the particular type of gonio lens in which the geometric reference member is applied.

In accordance with one aspect of the invention, the geometric reference member is applied over a background, and the color of the geometric reference member is chosen to be in contrast with the color of the background. The background and/or the geometric reference member may include fluorescent material so as to emit light in a contrasting color relative to each other.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1C are respective bottom view, cross-sectional view, and perspective view of the gonio lens with geometric reference constructed in accordance with an embodiment of the present invention;

DETAILED DESCRIPTION

Figure 2:
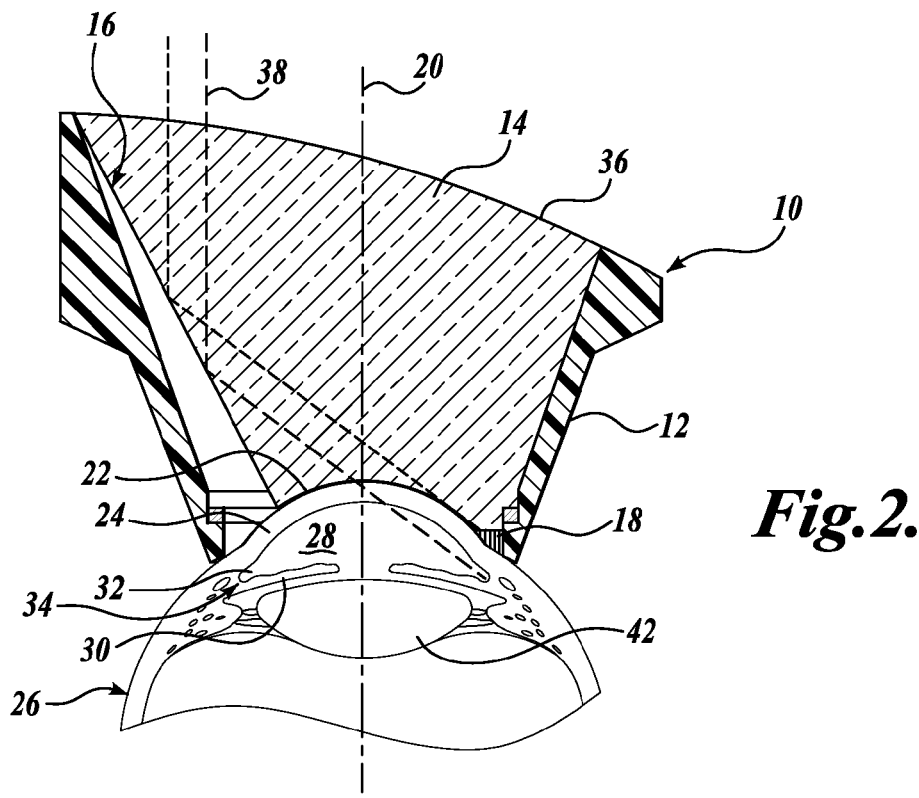
FIG. 2 is a longitudinal cross-sectional view of the gonio lens of FIGS. 1A-1C, similar to the cross-sectional view of FIG. 1B, shown in contact with the cornea of a patient's eye and illustrating the optical path for viewing the periphery of the anterior chamber.

Referring now to FIGS. 1A-1C, an embodiment of the gonio lens 10 of the present invention is housed in a frusto-conically shaped shell 12. Housed within the shell 12 is a contact lens element 14, a minor 16, and a geometric reference member 18.

Referring additionally to FIG. 2, the contact lens element 14 has an optical axis 20, a concave posterior contact surface 22 that has a curvature that approximates the curvature of the cornea 24 of an eye 26 of a patient. The anterior chamber 28 of the eye is defined between the cornea 24 and the iris 30, and the periphery 32 of the anterior chamber defines the iridocorneal angle, i.e., the angle formed by the cornea 24 and the iris 30 of an eye. The trabecular meshwork 34 is located generally around the base of the cornea 34.

The contact lens element 14 further has an anterior surface 36 that is offset in an anterior direction from the concave posterior contact surface 22. The anterior surface 36 may be curved so as to provide magnification, as shown, or may be plano. The minor 16 is provided in association with the contact lens element 14, in a position offset from the optical axis 20 of the contact lens element 14. The mirror 16 includes a planar surface that is angled away from the optical axis 20 of the contact lens element 14 as the planer surface extends in an anterior direction. The mirror 16 receives light rays 38 from the periphery 32 of the anterior chamber and reflects those rays in a generally anterior direction toward the observer. As one skilled in the art would appreciate, the minor 16 having a planar surface may be replaced with any suitable reflective surface, such as a prism facet. As used herein, the term minor means any optical surface configured to reflect the light from the periphery 32 of the anterior chamber 28.

The gonio lens 10 further includes the geometric reference member 18, which in the illustrated embodiment comprises a plurality of bar-shaped markings arranged along the periphery of a posterior end 40 of the gonio lens 10. The markings are spaced apart from each other to form a scale. The interval between the markings need not be constant and may vary to compensate for the curvature of the posterior end 40 on which the markings are applied. The geometric reference member 18 may be applied based on any suitable methods, such as by bonding the geometric reference member 18 to the radially interior surface of the posterior end 40 or by printing, painting or etching the markings that form the geometric reference member 18 on the interior surface of the posterior end 40 or on a background surface placed on the interior surface. In one embodiment, varying colors of material (e.g., plastic) may be laminated together and included in the gonio lens 10 to form the geometric reference member 18. For example, material (e.g., plastic) may be selectively cut away, with the cut-away portion(s) refilled with pigmented material (e.g., plastic), and included in the gonio lens 10. As a specific example, the material forming the contact lens element 14 may be selectively cut away, with the cut-away portion(s) refilled with pigmented material, such that the pigmented material (forming the marking(s) of the geometric reference member 18) remains after the concave posterior contact surface 22 is created and polished. Cut-away portions may have different shapes, and different colors (pigments) may be used for refilling, so as to form geometric reference members having various marking shapes and/or colors.

In one embodiment, the geometric reference member 18 may be constructed as a removable component, such as a ring, which is removably attached to the contact lens element 14 to form the gonio lens 10. Such a ring may be made of plastic or an elastomer such as silicone, and may be printed, painted, or etched with the marking(s) that forms the geometric reference member 18.

Figure 3:
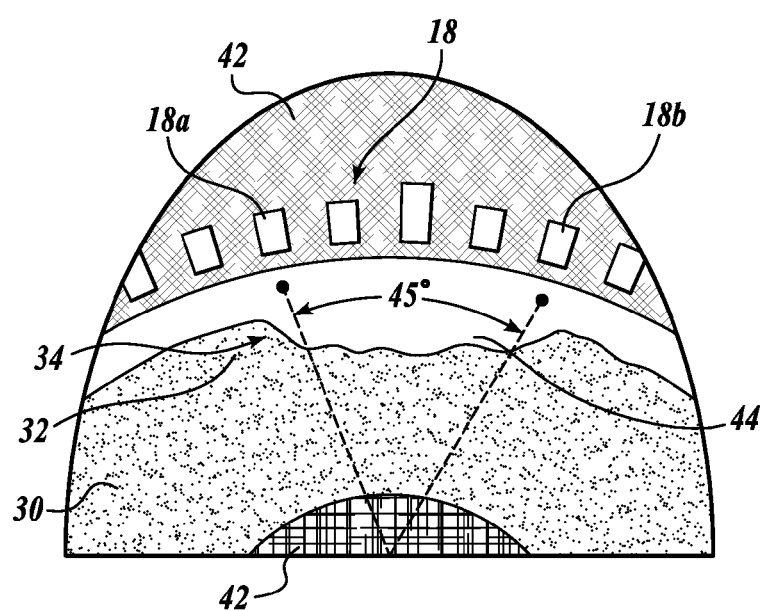
FIG. 3 schematically shows an image visible to the observer of the gonio lens of FIG. 2.

FIG. 3 schematically illustrates an image visible to the observer of the gonio lens 10 of FIG. 2. The observer can see, in addition to the pupil 42 and the iris 30 of the patient's eye, the periphery 32 of the anterior chamber including the trabecular meshwork 34 and the related adjacent structures of the eye. FIG. 3 shows a possible artifact area 44, i.e., a medically problematic area, in the periphery 32 of the anterior chamber. Using the geometric reference member 18, the observer can readily determine the size of the artifact area 44, which ranges between the first marking 18a and the second marking 18b. The observer can then readily translate the distance between these two markings into an actual dimension. As shown in FIG. 3, the field of view of the gonio lens 10 is preferably at least 45° and possibly about 90°, to permit easy observation of a wide area. The geometric reference member 18 may be in any suitable color and, preferably, in a color that is in high contrast to the color of its background 42. The background 42 may comprise the radially interior surface of the posterior end 40 of the gonio lens 10 or may be a separate sheet of material on which the geometric reference member 18 is placed. When the geometric reference member 18 is in generally white color, the background 42 is preferably in a bright, non-white color. The background 42 may comprise fluorescent material that emits light in a contrasting color relative to the color of the geometric reference member 18. Alternatively or additionally, the geometric reference member 18 itself may include fluorescent material that emits light in a contrasting color relative to the color of the background 42.

Since the image of the geometric reference member 18 is formed adjacent to an image of the periphery 32 of the anterior chamber 28 within the field of view of the gonio lens 10, the observer can readily determine the size or shape of any artifacts in the image of the periphery 32 of the anterior chamber or the relative distance between two or more points in such image. The two images are formed relative to each other (i.e., their respective image planes being sufficiently aligned relative to each other) such that the two images are simultaneously in focus to permit the observer to compare the two images.

Figure 4A:
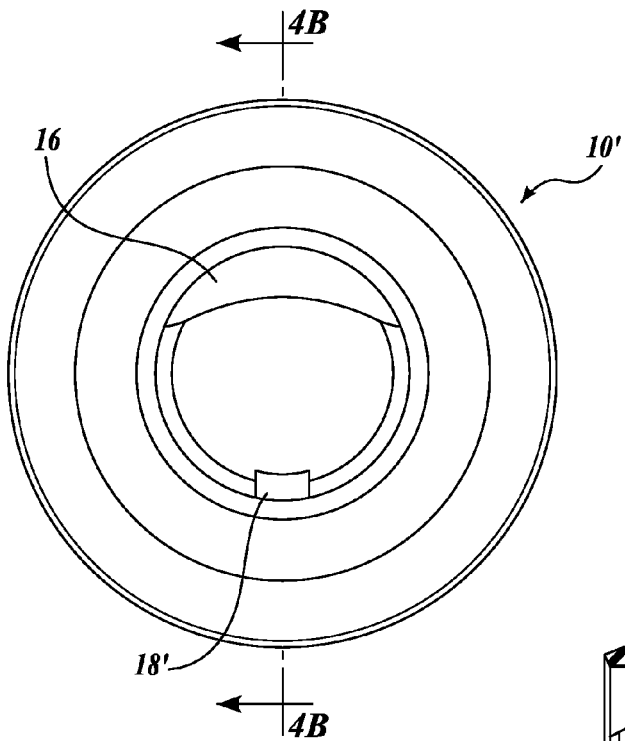
FIGS. 4A and 4B are respective bottom view and cross-sectional view of the gonio lens with geometric reference constructed in accordance with another embodiment of the present invention.
Figure 4B:
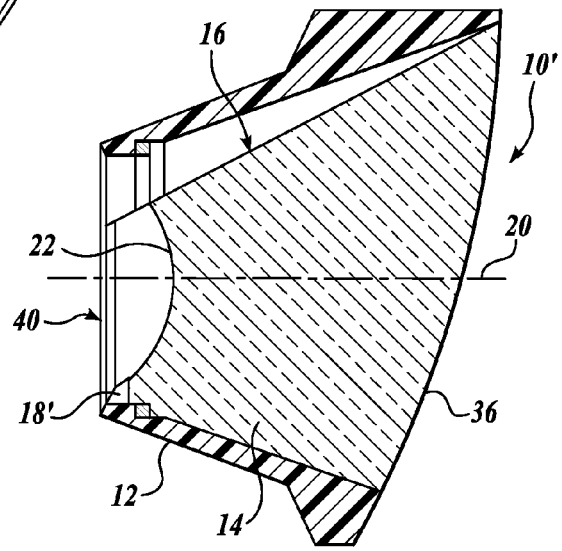
Figure 5:
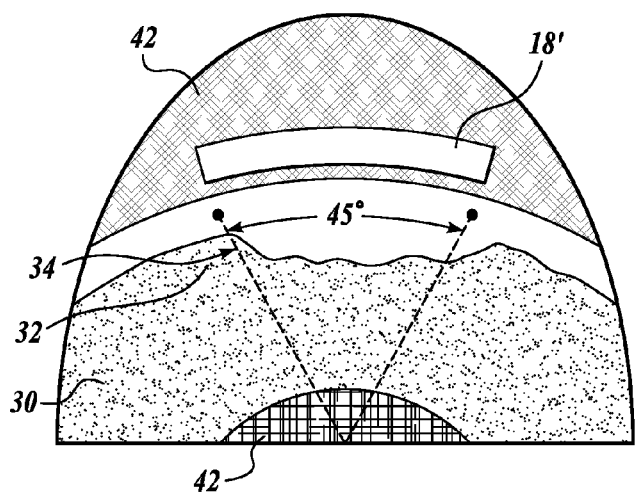
FIG. 5 schematically shows an image visible to the observer of the gonio lens of FIGS. 4A and 4B in contact with the cornea of a patient's eye.

FIGS. 4A and 4B illustrate a further embodiment of the gonio lens 10' constructed in accordance with the present invention. The gonio lens 10' is similar to the gonio lens 10 previously described, except that it includes a geometric reference member 18' configured in a generally bar shape. FIG. 5 schematically illustrates an image visible to the observer of the gonio lens 10' of FIGS. 4A and 4B in contact with the cornea of a patient's eye. As before, the observer can compare the image of the periphery 32 of the anterior chamber, including the trabecular meshwork 34, relative to the image of the geometric reference member 18', to thereby determine the size or shape of any artifacts in the image of the periphery 32 of the anterior chamber or the relative distance between two or more points in the image. In the illustrated embodiment, the length of the bar-shaped geometric reference member 18' is chosen so that it indicates 45° field of view of the gonio lens 10.

Figure 6A:
FIGS. 6A-6F illustrate six different embodiments of geometric reference that may be used in accordance with the present invention.
Figure 6B:
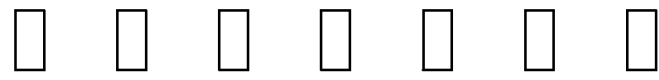
Figure 6C:
Figure 6D:
Figure 6E:
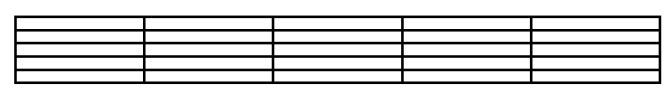
Figure 6F:
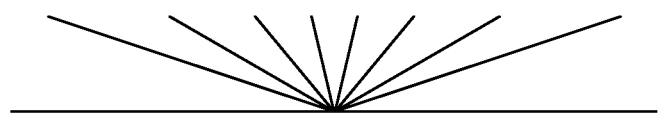
Figure 7A:
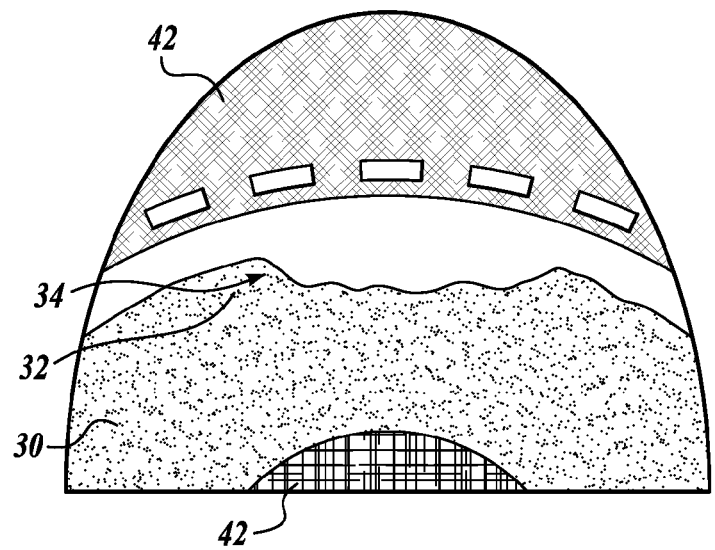
FIGS. 7A-7D schematically show an image visible to the observer of the gonio lens incorporating the geometric references of FIGS. 6C-6F, respectively.
Figure 7B:
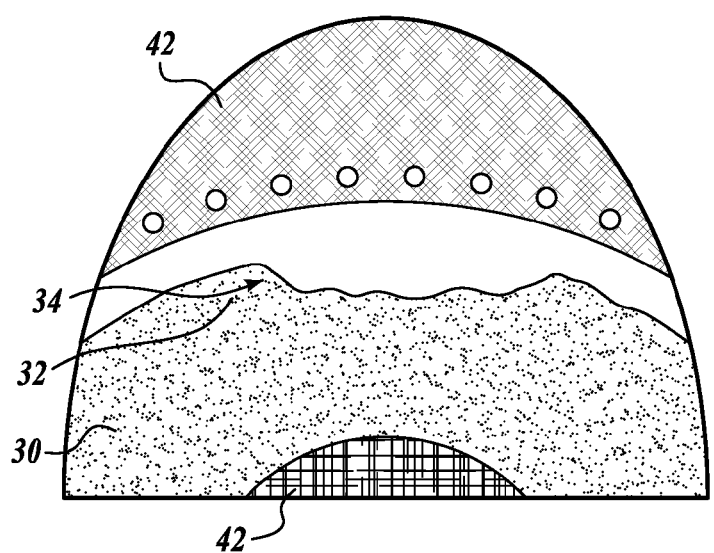
Figure 7C:
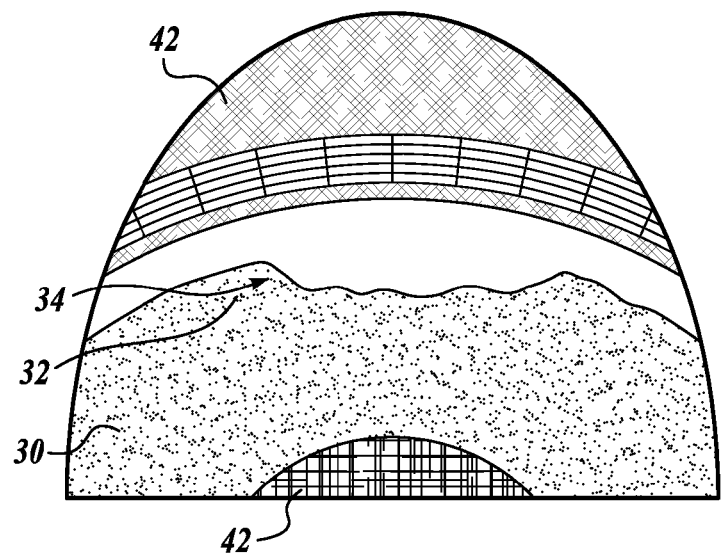
Figure 7D:
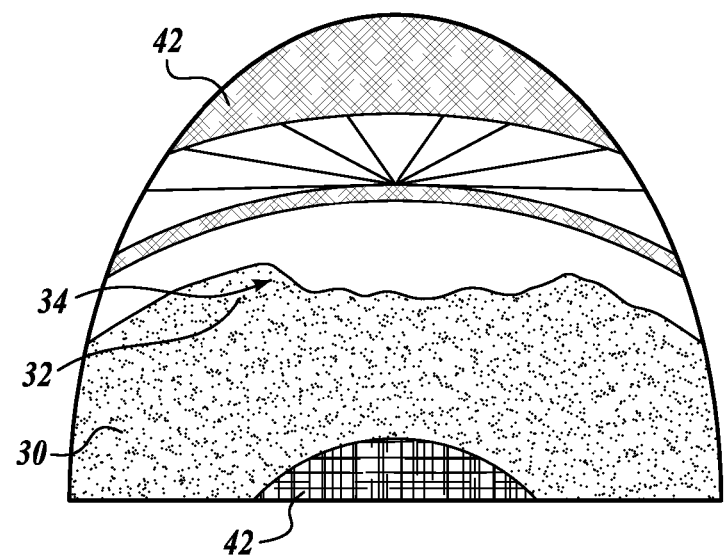

FIGS. 6A-6F illustrate still further examples of the geometric reference member 18 formed in accordance with various exemplary embodiments of the present invention. FIG. 6A shows a bar-shaped geometric reference member, similar to the one included in the gonio lens 10' of FIGS. 4A and 4B. FIG. 6B shows a geometric reference member comprising a horizontally-arranged series of vertical bars, similar to those included in geometric reference member 18 of FIGS. 1A-1C. FIG. 6C shows a geometric reference member comprising a horizontally-arranged series of horizontal bars. FIG. 6D illustrates a geometric reference member comprising a horizontally-arranged series of dots (or circles). FIG. 6E shows a geometric reference member comprising a rectangular grid. FIG. 6F shows a geometric reference member comprising a polar grid. All of these embodiments may function as a scale (e.g., linear scale, angular scale) to permit geometric measurements of the objects included in the image of the periphery of the anterior chamber.

FIGS. 7A-7D schematically illustrate an image visible to the observer of the gonio lens incorporating the geometric reference members formed in accordance with FIGS. 6C-6F, respectively. As before, the observer can compare the image of the periphery 32 of the anterior chamber, including the trabecular meshwork 34, relative to the image of the respective geometric reference member.

Figure 8A:
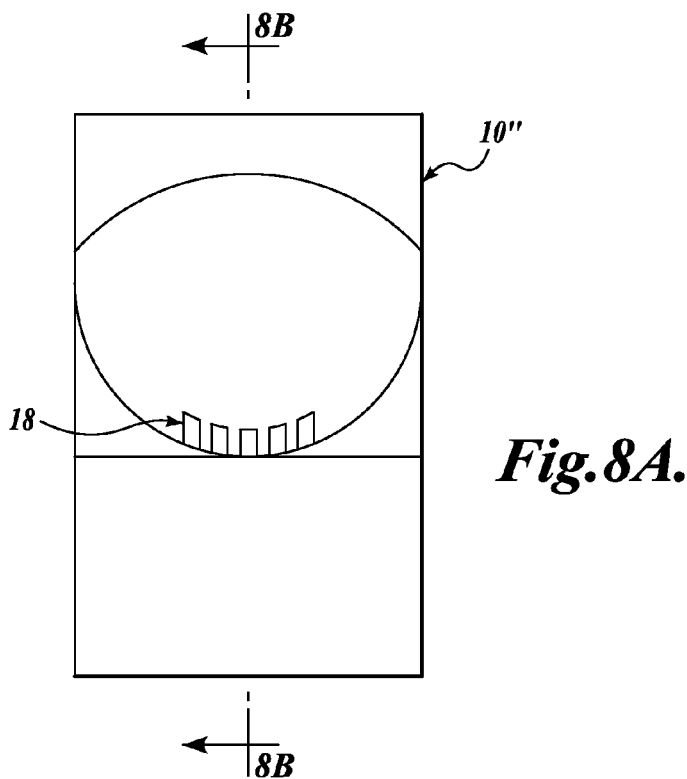
FIGS. 8A and 8B are respective bottom view and cross-sectional view of the gonio lens with geometric reference constructed in accordance with yet another embodiment of the present invention.
Figure 8B:
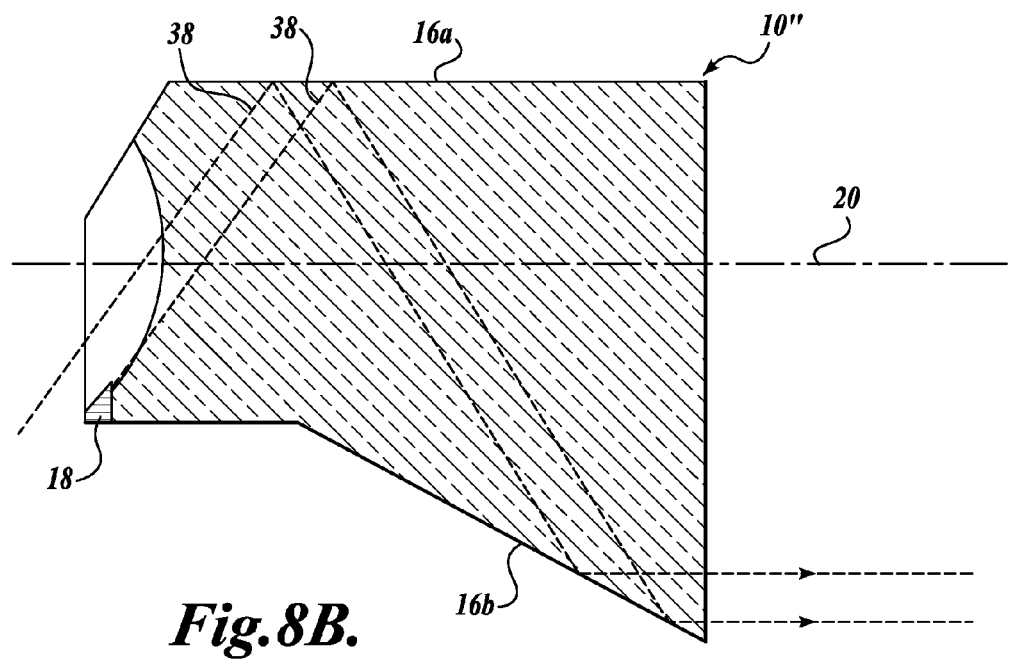

FIGS. 8A and 8B illustrate yet another embodiment of the gonio lens 10" constructed in accordance with the present invention. The gonio lens 10" is similar to the gonio lens 10 of FIGS. 1A-1C, except that it includes two minor surfaces 16a and 16b, instead of one. In operation, the first mirror surface 16a receives light rays 38 from the periphery of the anterior chamber and reflects those rays toward the second minor surface 16b, which in turn reflects the received light rays 38 in a generally anterior direction toward the observer. As before, the mirror surfaces 16a, 16b may be formed of any optical surface configured to reflect the light from the periphery of the anterior chamber, such as a prism facet. Also as before, with the present embodiment, the observer can compare the image of the periphery of the anterior chamber relative to the image of the geometric reference member 18, to thereby determine the size or shape of any artifacts in the image of the periphery of the anterior chamber or the relative distance between two or more points in the image.

Figure 9A:
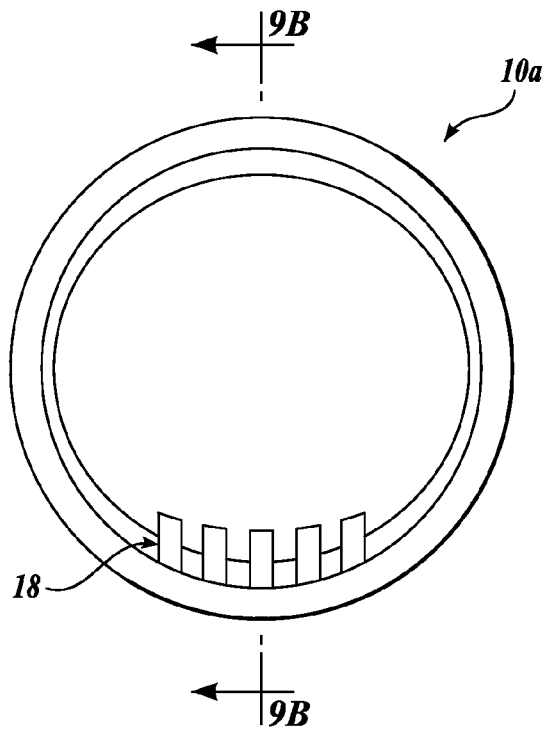
FIGS. 9A and 9B are respective bottom view and cross-sectional view of the gonio lens with geometric reference constructed in accordance with a further embodiment of the present invention.
Figure 9B:
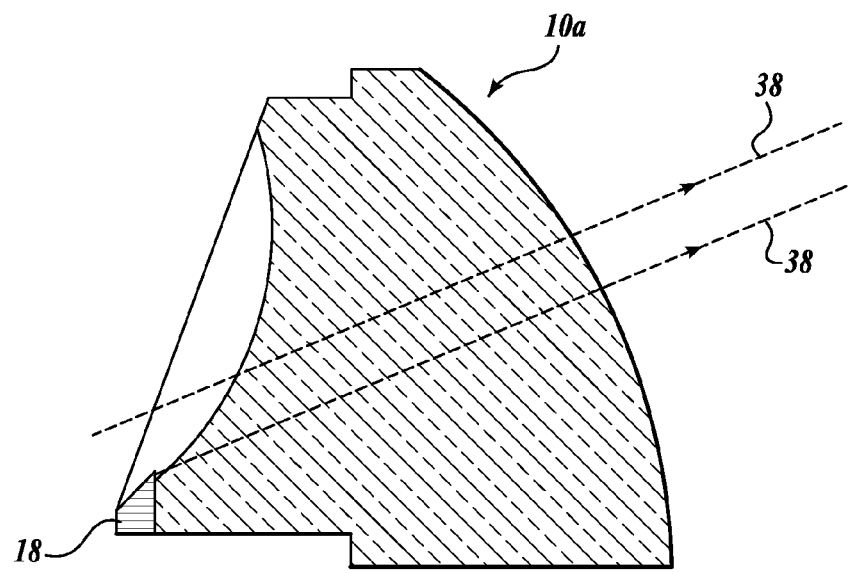

FIGS. 9A and 9B illustrate a further embodiment of the gonio lens 10a constructed in accordance with the present invention. The gonio lens 10a is similar to the gonio lens 10 of FIGS. 1A-1C, except that it does not include any mirror. In operation, the light rays 38 from the periphery of the anterior chamber propagate directly toward the observer. As before, with the present embodiment, the observer can compare the image of the periphery of the anterior chamber relative to the image of the geometric reference member 18, to thereby determine the size or shape of any artifacts in the image of the periphery of the anterior chamber or the relative distance between two or more points in the image.

One of ordinary skill will recognize that the geometric reference member may be applied in any type of gonio lens, having mirror(s) or no minors, to view the periphery of the anterior chamber, including but not limited to, diagnostic lenses and laser lenses (e.g., SLT goniolaser lenses). One of ordinary skill will also recognize that the specific configuration of a geometric reference member may be modified and adjusted depending on the particular type and purpose of a lens.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A gonio lens for use on an eye of a patient comprising:
    a contact lens element having an optical axis, a concave posterior contact surface and an anterior surface, said contact lens element having a mirror associated therewith and offset from the optical axis thereof, the mirror having a planar surface that is angled away from the optical axis as the planar surface extends in an anterior direction, and
    a geometric reference member provided near the concave posterior contact surface, the configuration and location of the geometric reference member being chosen to provide an image of the geometric reference member adjacent to an image of the periphery of the anterior chamber of the eye of a patient within a field of view of the contact lens element when the concave posterior contact surface of the contact lens element is in optical contact with a cornea of the eye of the patient, the two images being formed relative to each other such that they are simultaneously in focus.

2. The gonio lens of claim 1, wherein the geometric reference member is a scale.

3. The gonio lens of claim 2, wherein the scale includes linear markings.

4. The gonio lens of claim 3, wherein the linear markings comprise vertical bars that are horizontally arranged.

5. The gonio lens of claim 3, wherein the linear markings comprise horizontal bars that are horizontally arranged.

6. The gonio lens of claim 2, wherein the scale includes circular markings.

7. The gonio lens of claim 2, wherein the scale includes polar markings.

8. The gonio lens of claim 1, wherein the geometric reference member consists of a single marking.

9. The gonio lens of claim 8, wherein the single marking is a bar.

10. The gonio lens of claim 1, wherein the geometric reference member includes a rectangular grid.

11. The gonio lens of claim 1, wherein the geometric reference member includes a polar grid.

12. The gonio lens of claim 1, wherein the geometric reference member is applied over a background, the color of the geometric reference member is chosen to be in contrast with the color of the background.

13. The gonio lens of claim 12, wherein the background comprises fluorescent material.

14. The gonio lens of claim 1, wherein the geometric reference member comprises fluorescent material.

15. The gonio lens of claim 1, wherein the geometric reference member is constructed as a removable component, which is removably attached to the contact lens element.

16. The gonio lens of claim 15, wherein the geometric reference member is constructed as a ring, which is removably attached to the contact lens element.

17. A gonio lens for use on an eye of a patient, comprising:
    a contact lens element having an optical axis, a concave posterior contact surface and an anterior surface; and
    a geometric reference member provided near the concave posterior contact surface, the configuration and location of the geometric reference member being chosen to provide an image of the geometric reference member adjacent to an image of the periphery of the anterior chamber of the eye of a patient within a field of view of the contact lens element when the concave posterior contact surface of the contact lens element is in optical contact with a cornea of the eye of the patient, the two images being formed relative to each other such that they are simultaneously in focus.

18. The gonio lens of claim 17, wherein the geometric reference member comprises a scale.

19. The gonio lens of claim 17, wherein the geometric reference member comprises fluorescent material.

20. The gonio lens of claim 17, wherein the geometric reference member is constructed as a removable component, which is removably attached to the contact lens element.

* * * * *